US009610797B2

(12) United States Patent
Boisdevesys

(10) Patent No.: US 9,610,797 B2
(45) Date of Patent: Apr. 4, 2017

(54) ERGONOMIC AND VERSATILE WRITING INSTRUMENT

(71) Applicant: SOCIETE BIC, Clichy (FR)

(72) Inventor: David Boisdevesys, Vitry sur Seine (FR)

(73) Assignee: Societe BIC, Clichy (FR)

( * ) Notice: Subject to any disclaimer, the term of this patent is extended or adjusted under 35 U.S.C. 154(b) by 474 days.

(21) Appl. No.: 14/024,200

(22) Filed: Sep. 11, 2013

(65) Prior Publication Data

US 2014/0072359 A1 Mar. 13, 2014

(30) Foreign Application Priority Data

Sep. 11, 2012 (FR) ..................................... 12 58506

(51) Int. Cl.

| | |
|---|---|
| ***A61B 17/32*** | (2006.01) |
| ***B43K 19/02*** | (2006.01) |
| ***B43K 23/00*** | (2006.01) |
| ***B43K 5/00*** | (2006.01) |
| ***B43K 7/00*** | (2006.01) |
| ***G09B 11/02*** | (2006.01) |
| ***B43K 23/008*** | (2006.01) |
| ***B43K 24/02*** | (2006.01) |
| ***B43K 24/06*** | (2006.01) |

(52) U.S. Cl.
CPC .......... *B43K 23/008* (2013.01); *B43K 24/023* (2013.01); *B43K 24/06* (2013.01)

(58) Field of Classification Search
CPC .... B43K 23/008; B43K 24/06; B43K 24/023; B43K 21/02; B43K 8/003; B43K 7/005; B43K 5/165; B43K 5/005; B43K 15/00; B43K 7/12; A46B 5/02
USPC ....................................... 401/6, 117, 198, 88
See application file for complete search history.

(56) References Cited

U.S. PATENT DOCUMENTS 564,178 A 7/1896 Ahrens
836,652 A 11/1906 Rosdahl
1,861,241 A * 5/1932 Putnam .................. B43K 5/005 15/443

(Continued)

FOREIGN PATENT DOCUMENTS

CN 2685093 Y 3/2005
CN 2818160 Y 9/2006

(Continued)

OTHER PUBLICATIONS

French Preliminary Search Report dated Jan. 7, 2013 corresponding to French Patent Application 1258506, 2 pp.

*Primary Examiner* — Mark A Laurenzi
*Assistant Examiner* — Thomas M Abebe
(74) *Attorney, Agent, or Firm* — Ohlandt, Greeley, Ruggiero & Perle, L.L.P.

(57) ABSTRACT

A writing instrument has a front body with an ergonomic grasping segment asymmetrical relative to a first longitudinal plane, and a rear body asymmetrical relative to a second longitudinal plane. The rear body is capable of rotating relative to the front body about a longitudinal axis corresponding to a line of intersection between the first longitudinal plane and the second longitudinal plane, between a position adapted to gripping with a right hand and a position adapted to gripping with a left hand. The present invention also relates to a method of using this writing instrument.

16 Claims, 5 Drawing Sheets

(56) References Cited

U.S. PATENT DOCUMENTS

| | | | | | |
|---|---|---|---|---|---|
| 2,263,885 | A * | 11/1941 | McGauley | A46B 5/02 | 15/143.1 |
| 2,664,858 | A * | 1/1954 | Lepkowski | B43K 5/18 | 401/231 |
| 4,076,427 | A * | 2/1978 | Anderson | A46B 5/02 | 401/198 |
| 4,149,811 | A * | 4/1979 | Coffman | A46B 5/02 | 15/443 |
| 4,529,328 | A * | 7/1985 | Wacha | B43K 7/005 | 401/116 |
| 4,585,364 | A * | 4/1986 | Liaw | B43K 29/087 | 346/143 |
| 5,143,463 | A * | 9/1992 | Pozil | G09B 11/02 | 15/443 |
| 5,143,465 | A * | 9/1992 | Hou | F21V 33/0048 | 362/118 |
| 5,228,794 | A * | 7/1993 | Hochstetler | B43K 23/004 | 401/6 |
| 5,527,124 | A * | 6/1996 | Kolaric | B43K 5/005 | 401/109 |
| 6,086,445 | A * | 7/2000 | Zawitz | B43K 5/005 | 242/588.1 |
| 6,648,536 | B1 * | 11/2003 | Bellue | B43K 19/02 | 16/430 |
| 7,147,392 | B2 * | 12/2006 | Bedhome | B43K 1/006 | 401/29 |
| 7,661,896 | B2 * | 2/2010 | Zawitz | B43K 5/005 | 401/6 |
| D667,054 | S * | 9/2012 | Dyer | D19/178 | |
| 9,022,676 | B2 * | 5/2015 | Kalif | B43K 29/00 | 401/6 |
| 2005/0232680 | A1 | 10/2005 | Schulken | | |
| 2006/0045604 | A1 * | 3/2006 | Fukui | B25G 1/00 | 401/6 |
| 2006/0228156 | A1 * | 10/2006 | Chan | B43K 5/005 | 401/107 |
| 2007/0172301 | A1 * | 7/2007 | Rolion | B43K 24/06 | 401/117 |
| 2007/0196158 | A1 * | 8/2007 | Roche | B26B 5/00 | 401/7 |
| 2008/0295255 | A1 * | 12/2008 | Whitehead | B25G 1/102 | 7/167 |
| 2009/0175672 | A1 * | 7/2009 | Killion | B43K 23/001 | 401/100 |
| 2011/0222952 | A1 * | 9/2011 | Gueret | A45D 34/042 | 401/8 |
| 2015/0296958 | A1 * | 10/2015 | Holloway | A45D 40/06 | 401/78 |
| 2016/0129722 | A1 * | 5/2016 | Csokmay | B43K 8/003 | 401/6 |

FOREIGN PATENT DOCUMENTS

| | | | |
|---|---|---|---|
| CN | 200988368 | Y | 12/2007 |
| CN | 101367306 | A | 2/2009 |
| CN | 101905595 | A | 12/2010 |
| CN | 201721178 | U | 1/2011 |
| DE | 102010060096 | A1 | 4/2012 |
| EP | 0913270 | A1 | 5/1999 |
| EP | 1800894 | A1 | 6/2007 |
| FR | 389129 | | 9/1908 |
| FR | 2819217 | A1 | 7/2002 |
| FR | 2856013 | A1 | 12/2004 |
| JP | 8300878 | | 11/1996 |
| JP | 10100582 | | 4/1998 |
| JP | 2001162985 | A | 6/2001 |
| JP | 2006056035 | A | 3/2006 |
| JP | 3126015 | | 10/2006 |
| JP | 2007190843 | A | 8/2007 |
| JP | 2011093269 | A | 5/2011 |
| JP | 2011093270 | A | 5/2011 |
| WO | 0197653 | A1 | 12/2001 |
| WO | 2007121613 | A1 | 11/2007 |

* cited by examiner

ERGONOMIC AND VERSATILE WRITING INSTRUMENT

CROSS-REFERENCE TO RELATED APPLICATIONS

This application claims priority from French Patent Application No. 1258506 filed on Sep. 11, 2012. The disclosure of French Patent Application No. 1258506 filed on Sep. 11, 2012 is hereby incorporated by reference.

BACKGROUND OF THE INVENTION

The present invention relates to the field of writing instruments, and more particularly the ergonomics thereof.

In the present context <<writing instrument>> means any instrument for manually tracing writing on an adapted surface. Examples of writing instruments are for example pencils, pens, ballpoint or felt-tipped pens, and even adapted styluses. All these writing instruments typically have an elongated form for gripping a front part of the writing instrument between the tips of the thumb and at least one of the index and middle fingers, while a rear part is supported in the grasping angle between the thumb and the index finger to stabilise the writing instrument in the hand. To facilitate this grasping, in particular for school pupils when learning to write, different writing instruments of ergonomic design have been proposed.

Some of these ergonomic writing instruments, such as for example that disclosed in international patent application WO 01/97653, have a front body with an asymmetrical and ergonomic grasping segment relative to a first longitudinal plane, and an asymmetrical rear body relative to a second longitudinal plane, different to the first longitudinal plane. The grasping segment is adapted to be gripped between the tips of the fingers, while the asymmetry of the rear body better matches the form of the grasping angle, that is, the space between the thumb and the index finger of one hand.

However, one disadvantage of such ergonomic writing instruments is that due to their asymmetry they can be adapted to usage with the left hand or right hand only. Different instruments must therefore be produced for right-handed and left-handed people, with everything this involves in terms of production and storage costs, as well as disadvantages for users.

SUBJECT MATTER AND SUMMARY OF THE INVENTION

The present invention sets out to overcome these disadvantages. In particular it is the objective of the invention to propose a writing instrument comprising a front body with an ergonomic grasping segment asymmetric relative to a first longitudinal plane, and a rear body asymmetric relative to a second longitudinal plane but which allows use thereof with either the right hand or the left hand.

In at least one embodiment, this objective is achieved through the fact that the rear body is able to rotate relative to the front body about a longitudinal axis corresponding to a line of intersection between the first longitudinal plane and the second longitudinal plane, between a position adapted to gripping with a right hand and a position adapted to gripping with a left hand.

Because of these arrangements, the form of the writing instrument can be adapted to ergonomic usage alternatively with the left hand or with the right hand, such that the ergonomics of this instrument no longer conflict with its versatility.

To separate the index and the thumb on the ergonomic grasping segment, on one side of said first longitudinal plane the latter can have a rib oriented longitudinally and radially projecting relative to a grasping surface of said segment. In particular, this rib can project by at least 2 mm relative to the grasping surface of said segment. This rib can make learning to write easier, helping students to correctly position their fingers on the ergonomic grasping segment. Also, it ensures more stable gripping of the writing instrument.

The ergonomic grasping segment can also have a stop flange for fingers in the direction of a front end of the front body, for example at a distance of at least 10 mm from this distal end, to ensure a sufficient distance of the fingers relative to the writing surface for the purpose of cleaning the field of vision of the user, which is not only advantageous when students are learning to write, but makes it more comfortable for other users. For better ergonomics, this flange can especially be inclined relative to the longitudinal axis.

To make gripping of the writing instrument more comfortable, said ergonomic grasping segment can also have a supple grasping surface, preferably overmoulded on the front body.

To better stabilise the writing instrument in the grasping angle of the hand, the rear body can comprise, on one side of said second longitudinal plane, a concave surface configured to be supported on the base of the index finger.

It is generally known to equip writing instruments with a retractable writing tip thereby making it possible to retract the writing tip in particular when the instrument is not in use, to avoid staining, drying of the writing tip, etc. Among the different mechanisms used for retracting and extending the writing tip, persons skilled in the art have particular knowledge of mechanisms actuated by relative rotation of the two parts of the writing instrument.

If the writing instrument comprises a front body and a rear body which can turn relatively relative to each other about a longitudinal axis between a position adapted to gripping with a right hand and a position adapted to gripping with a left hand, this writing instrument could also comprise a writing point, and a retraction and extension mechanism of the writing point, actionable by relative rotation of the front body and the rear body, and configured such that the writing point is retracted into the front body when the rear body and the front body are in an intermediate position between the position adapted to gripping with the right hand and the position adapted to gripping with the left hand, and projecting beyond a front end of the front body when the rear body and the front body are in the position adapted to gripping with the right hand or in the position adapted to gripping with the left hand. In this way, the act of turning the rear body relative to the front body to adapt it to usage with the right hand or the left hand will simultaneously help move the writing point to its projecting position in which the writing instrument can be used.

In particular, this retraction and extension mechanism may comprise a cam surface secured in rotation with one of the said front and rear bodies, and an element secured in rotation with the other of said front and rear bodies and in contact with said cam surface, the cam surface or said element in contact with the cam surface being capable of moving within the writing instrument along said longitudinal axis and being secured to the writing tip at least in translation along the longitudinal axis. The cam surface therefore allows the conversion of the rotational movement between front and rear bodies to a translational movement of the writing tip along the longitudinal axis. To ensure the same extension movement of the writing tip during rotation in each direction from the said intermediate position, this cam surface may be symmetrical. In addition, to ensure the contact of the second part against the cam surface, the retraction and extension mechanism may also comprise an elastic element arranged so as to push the second part against the cam surface.

A further aspect of the present invention concerns the assembly of the writing instrument. Since the front body and the rear body will frequently be rotated relative to one another in both directions of rotation about the longitudinal axis throughout the lifetime of the writing instrument, a screw connection does not appear to be adapted. However to provide a robust connection, easy to implement industrially and allowing relative rotation of the front and rear bodies about the longitudinal axis, this writing instrument may further comprise a tubular piece axially joining together i.e. in the direction of the longitudinal axis, the front body and the rear body via elastic snap-fit. Snap-fit (or snap-lock) is a mode of assembling by engagement two parts and elastic deformation (in general local deformation e.g. of a tab). When the two parts are engaged in the snap-fit position, the parts have generally resumed their initial shape and are not elastically deformed anymore (or are less elastically deformed). When the two parts are engaged in each other in the snap-fit position they cooperate with each other so as to resist and even block the relative movements of the said parts in the direction of disengagement (opposite direction to the engaging direction). In the snap-fit position the two parts may also cooperate so as to resist and even block their relative movements in the direction of further engagement, beyond the snap-fit position. In particular, this tubular piece may have shoulders opposite corresponding shoulders of the front and rear bodies for axial retaining of said tubular piece relative to the front and rear bodies. This configuration simplifies the mechanical assembling of the writing instrument, which can therefore be assembled by mere axial engaging of the front and rear bodies, in opposite direction, against the tubular piece. The tubular piece may have some degree of radial elasticity to allow snap-fit, its radial shoulders coming to bear against those of the front body and rear bodies after its elastic return so as to retain the latter axially. This tubular piece may in particular be received in the writing instrument, thereby allowing a non-apparent connection between the front body and the rear body.

The tubular piece may be secured in rotation with one of the said front and rear bodies and have two rotation stops relative to the other of said front and rear bodies. This part may therefore be used to limit relative rotation between the two bodies.

To facilitate elastic snap-fit, this elastic part may comprise a longitudinal slot. In this case it may also, in this longitudinal slot, receive a rib secured to one of said front or rear bodies. The longitudinal slot can therefore be used to lock the tubular piece in rotation relative to one of said front or rear bodies. In addition, the rib may be press-fit into the longitudinal slot so as to cause radial expansion of the tubular piece and the engaging of the tubular piece with inner shoulders into at least one of the front or rear bodies to ensure the axial connection between the front and rear bodies via the tubular piece.

The present invention also concerns a method of use of this writing instrument whereby the ergonomic grasping segment is held between the tips of the thumb and at least one of the index and middle fingers in one same hand, and the rear body is rotated relative to the front body towards the position adapted to gripping with a right hand or towards the position adapted to gripping with a left hand depending on the hand used, so as to ensure the supporting of the rear body in the grasping angle between the index finger and the thumb.

BRIEF DESCRIPTION OF THE DRAWINGS

The invention will be more clearly understood and its advantages will emerge more clearly from the following detailed description of an embodiment illustrated by way of non-limiting example. The description refers to the attached diagrams, in which.

DETAILED DESCRIPTION OF THE INVENTION

Figure 1:
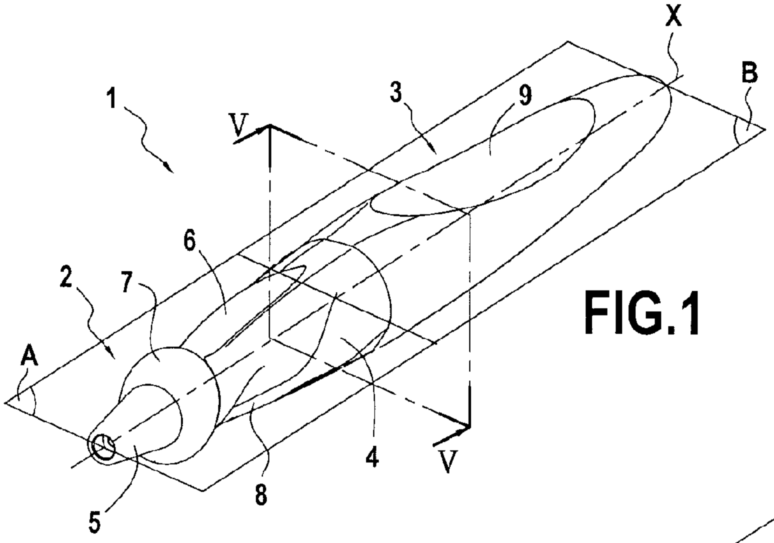
FIG. 1 is a perspective view of a writing instrument according to an embodiment.
Figure 2:
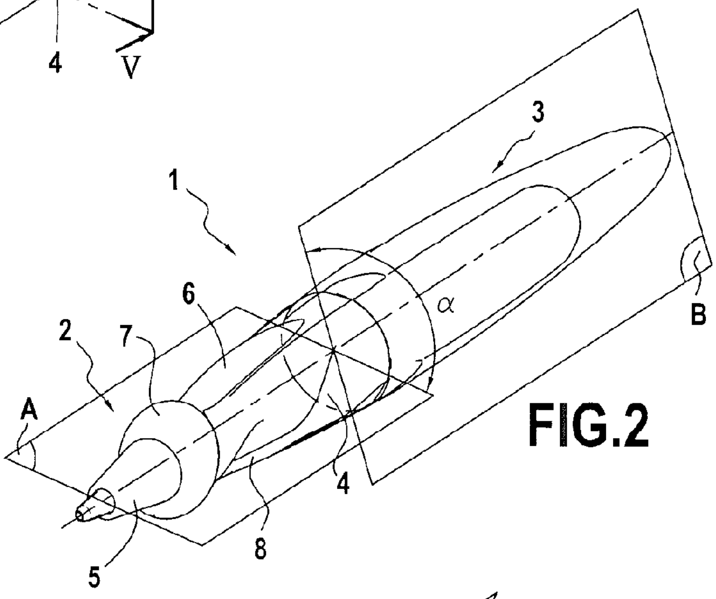
FIG. 2 is a perspective view of the writing instrument of FIG. 1 in a position adapted to usage with the right hand.
Figure 3:
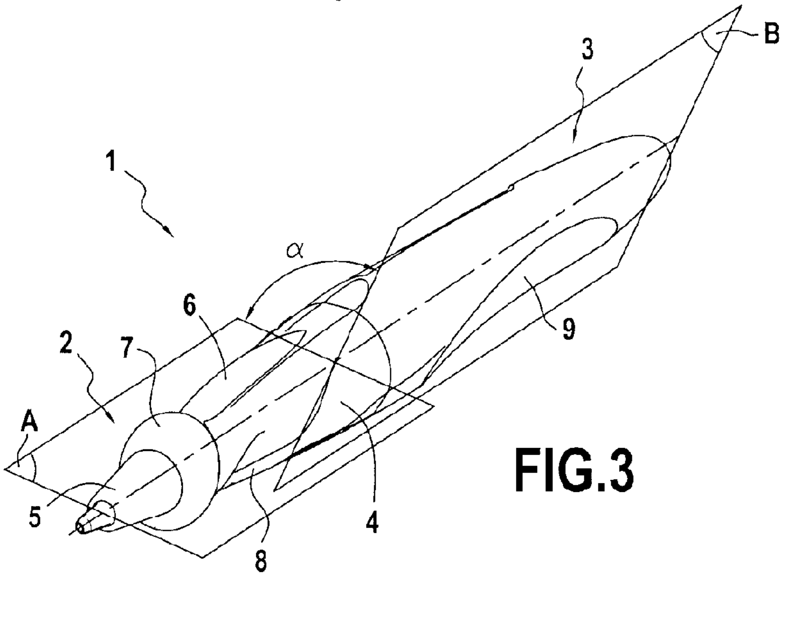
FIG. 3 is a perspective view of the writing instrument of FIGS. 1 and 2 in a position adapted to usage with the left hand.

The general arrangement of a writing instrument 1 is illustrated in FIGS. 1 to 3. This writing instrument 1, which in the illustrated embodiment more specifically takes the form of a ballpoint, comprises a front body 2 and a rear body 3 which can turn relative to each other about a longitudinal axis X.

The front body 2 comprises two parts: an ergonomic grasping segment 4 and an end part 5 forming a distal end of this front body 2. The segment 4 is asymmetrical relative to a longitudinal plane A, as it has especially, on a single side of this longitudinal plane A, a radially projecting rib 6. During use of the instrument 1, this rib 6 operates as a key to make gripping easy by separating the thumb from the index finger. The segment 4 also has a radially projecting flange 7, opposing the fingers in the direction of the front end of the front body 2, and in this way also making it easier for the index and middle fingers and thumb to grip round the segment 4. In the embodiment illustrated, this flange 7 is inclined in an axial direction for better gripping comfort of the segment 4. The segment 4 also has an overmoulded grasping surface 8, made of material suppler than the rest of the segment 4. This grasping surface 8, slightly concave, can also have a texture in relief or projecting for securer gripping. The end part 5 has a conical external surface and a thread complementary to an internal thread inside the segment 4 for fixing it to the front end of the segment 4.

The rear body 3 is asymmetrical relative to a longitudinal plane B, as it has especially, on a single side of this longitudinal plane B, a concave support surface 9 to facilitate support of the rear body on the base of the index finger in the grasping angle of the hand of the user. However, depending on whether the hand being used is the right hand or the left hand, the index finger will be to one side or the other of the rib 6. To adapt the instrument 1 to usage with the right hand or the left hand, the rear body 3 can turn relative to the front body 2, about the longitudinal axis X, between the position illustrated in FIG. 2, which is adapted to use with the right hand with the surface concave 9 to the right of the rib 6, and the position illustrated in FIG. 3, which is adapted to use with the left hand with the concave surface 9 to the left of the rib 6.

Between these two positions, the longitudinal planes A and B turn relative to each other about their line of intersection along the longitudinal axis X. As a consequence, the instrument 1 can also adopt the intermediate position illustrated in FIG. 1, between the positions of FIGS. 2 and 3, in which the longitudinal plane A of the front body 2 coincides with the longitudinal plane B of the rear body 3. In the embodiment illustrated, the instrument 1 comprises a retractable writing point 10, and a retraction and extension mechanism of this writing point 10 which is actionable by relative rotation of the front body and rear body 2, 3, and configured such that the writing point 10 is retracted into the front body 2 when the front and rear bodies 2, 3 are in the intermediate position illustrated in FIG. 1, and projecting beyond the front end of the front body 2 when the front and rear bodies 2, 3 are in the positions illustrated in FIGS. 2 and 3. The angle of rotation a of the rear body 3 relative to the front body 2, between the intermediate position illustrated in FIG. 1 and each of the positions illustrated in FIGS. 2 and 3 can be 120°, for example.

Figure 4:
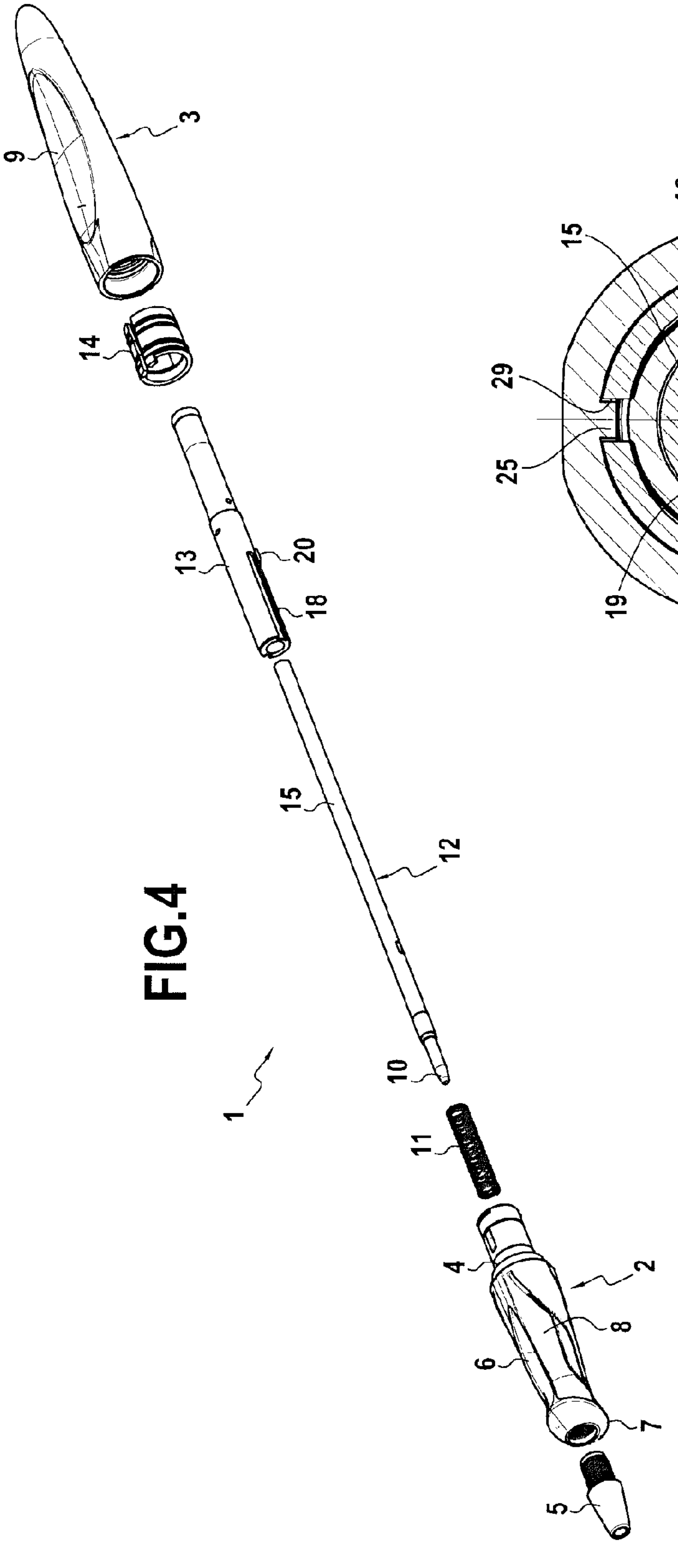
FIG. 4 is an exploded perspective of the writing instrument of the preceding Figures.

FIG. 4 illustrates an exploded perspective of the instrument 1, showing its internal components. In this way, inside the instrument 1 illustrated the latter contains an elastic element 11 in the form of a helical spring, a standard ballpoint refill 12, a slide 13 and a tubular piece 14. The refill 12 comprises the writing point 10 and an ink tank 15 and is received inside the slide 13, which is open to the front and at least partially closed to the rear. The elastic element 11, supported against the internal face of the end part 5 at the front end of the front body 2, presses the refill 12 against the bottom of the slide 13.

Figure 5:
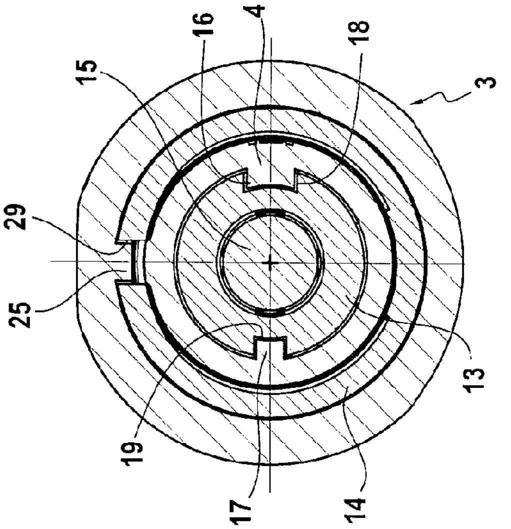
FIG. 5 is a view in transversal section of the writing instrument of FIG. 1 in the plane V-V.

As is evident from FIG. 5, which is a transversal section of the instrument 1 along the plane V-V of FIG. 1, ribs 16, 17 on the internal surface of the front body 2 cooperate with grooves 18, 19 on the external surface of the slide 13, to have the slide 13 connected to the front body 2 in rotation about the longitudinal axis X, and enable axial displacement of the slide 13 along the longitudinal axis X.

Figure 6:
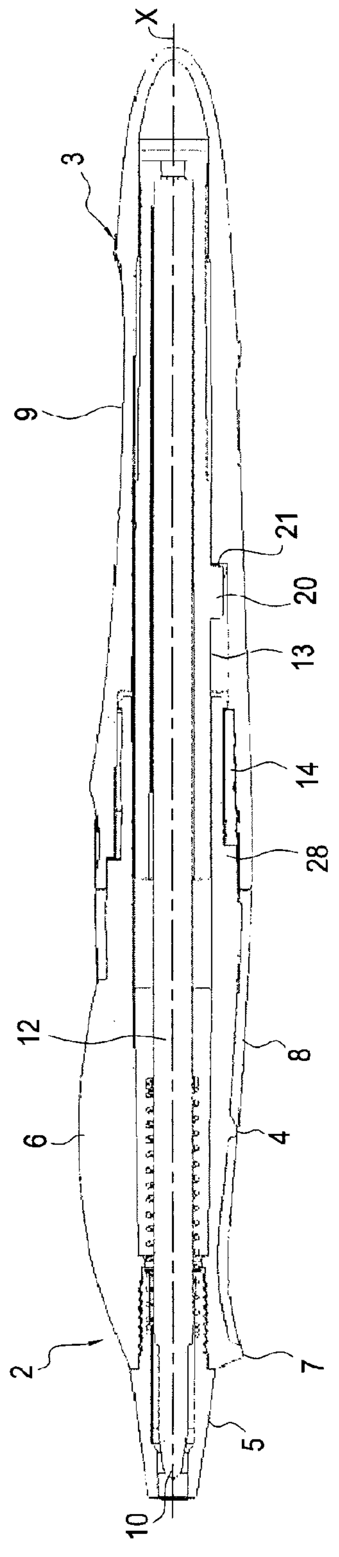
FIG. 6 is a view in longitudinal section of the writing instrument of the preceding Figures in the position of FIG. 1.
Figure 7:
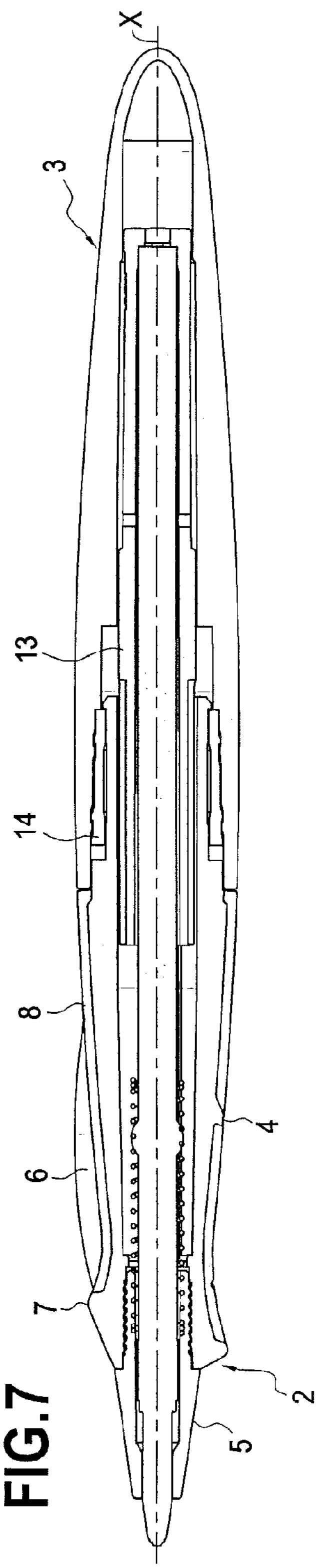
FIG. 7 is a view in longitudinal section of the writing instrument of the preceding Figures in the position of FIG. 3.

The slide 13 also has a finger 20 on its external surface. As is evident from FIG. 6, this finger 20 is in contact with a cam surface 21 formed in the internal surface of the rear body 3 and with it constitutes an extension and retraction mechanism of the writing point 10. The cam surface 21 has a helical contour capable of pushing the finger 20 to the front when the rear body 3 turns in one or the other direction from the intermediate position illustrated in FIG. 1. As the finger 20 is connected to the writing point 10 via the slide 13 and the refill 12, rotation of the rear body 3 in one or the other direction about the longitudinal axis X relative to the front body 2 will cause displacement of the writing point 10 between its retracted position, illustrated in FIG. 6, and its writing position, illustrated in FIG. 7. In the retracted position illustrated in FIG. 6 the writing point 10 is received in the front body 2, and more specifically, in the end part 5 in the illustrated embodiment. In the writing position, illustrated in FIG. 7, the writing point 10 projects beyond the front end of the front body 2.

Figure 8:
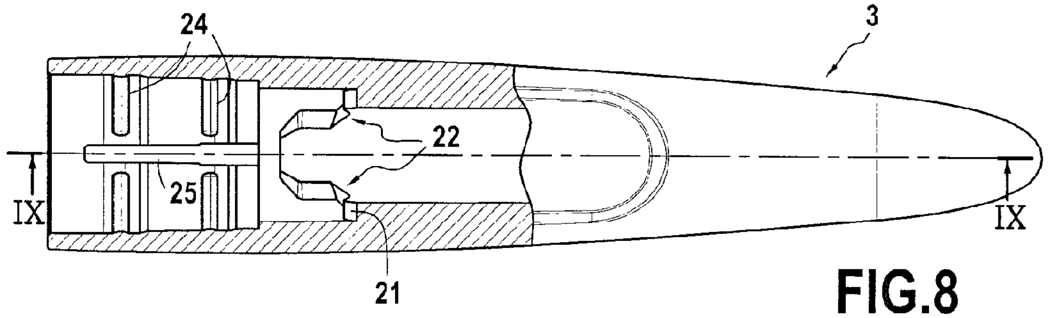
FIG. 8 is an exposed view of a rear body of the writing instrument of the preceding Figures.
Figure 9:
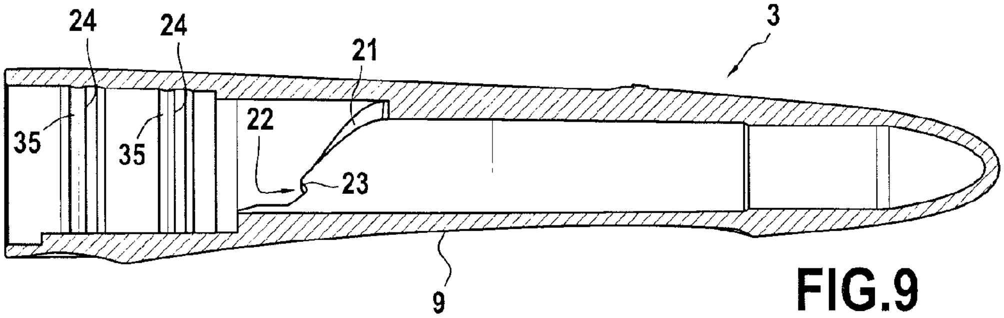
FIG. 9 is a view in longitudinal section of the rear body of FIG. 8 along the line IX-IX.

The cam surface 21 is more clearly visible in FIGS. 8 and 9, respectively illustrating a partial cutaway of the rear body 3, and a partial longitudinal section along a plane IX-IX perpendicular to the plane B. This shows in particular how the cam surface 21 is symmetrical relative to the longitudinal plane B so as to actuate the same extension movement of the writing point 10 when the rear body 3 is turned in one or the other direction from the intermediate position illustrated in FIGS. 3 and 6. Also, on each side this cam surface has a notch 22 at the end designed to hook the finger 20 and in this way block the writing point 10 in its writing position. However, the angle of inclination of the inner edge 23 of each notch 22 is such that it offers only slight resistance to rotation of the rear body 3 when the user turns it, relative to the front body 2, from this position to its intermediate position to retract the writing point 10 into the front body 2.

Figure 10:
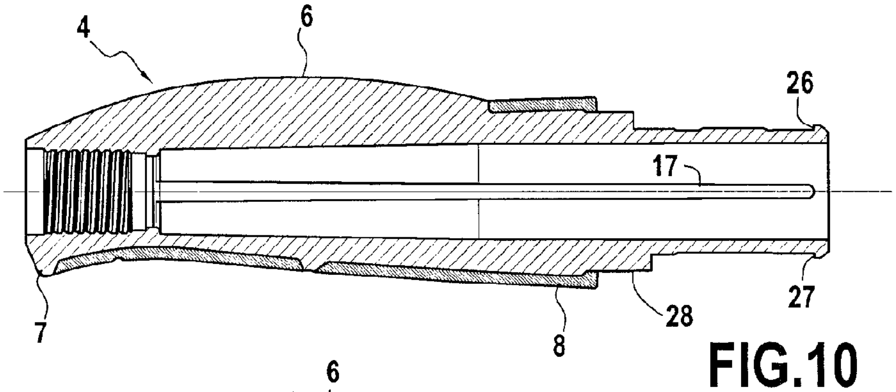
FIG. 10 is a view in longitudinal section of a front body of the writing instrument of the preceding Figures.
Figure 11:
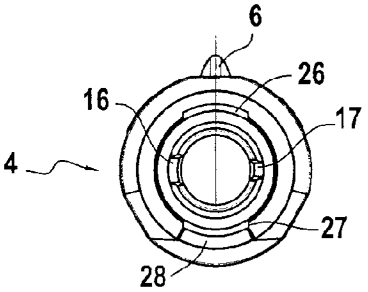
FIG. 11 is a rear view of the front body of FIG. 10.
Figure 12:
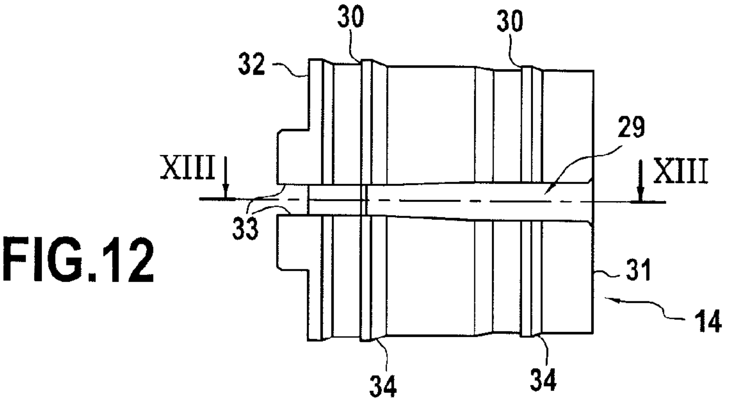
FIG. 12 is a plan view of a tubular piece designed to connect said front and rear bodies.
Figure 13:
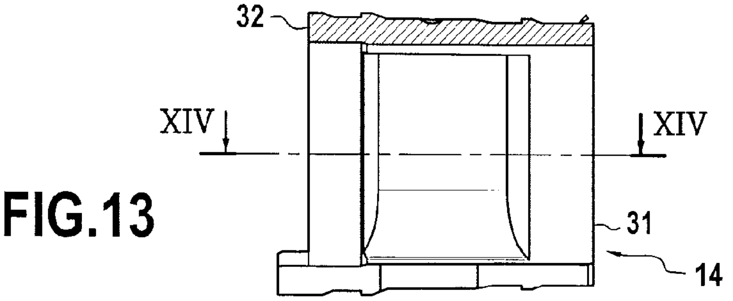
FIG. 13 is a view in longitudinal section of the tubular piece of FIG. 12 along the line XIII-XIII.
Figure 14:
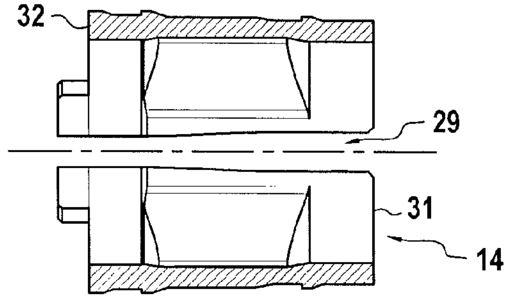
FIG. 14 is a view in longitudinal section of the tubular piece of FIG. 13 along the line XIV-XIV.

The rear body 3 also comprises, on its internal surface, radial shoulders 24 and a longitudinal rib 25 designed to cooperate with the tubular piece 14. As illustrated in FIGS. 10 and 11, on its rear end the segment 4 also has lips 26, 27 designed to cooperate with the tubular piece 14, as well as a rotation stop 28. This tubular piece 14 is illustrated in greater detail in FIGS. 12 to 14. These Figures show how the latter has a longitudinal slot 29. On the one hand, because of this longitudinal slot, the tubular piece 14 is more easily deformable elastically in a radial plane. But this slot 29 is also capable of taking up the rib 25 of the rear body 3 so as to cooperate with the latter to have the tubular piece 14 connect to the rear body in rotation, as illustrated in particular in FIG. 5. The width of the slot 29 when the tubular piece 14 is free of stress is however less than that of the rib 25, such that when the rib 25 is introduced to the slot 29, it causes radial expansion of the tubular piece 14. FIGS. 12 to 14 also show how the tubular piece 14 has radial shoulders 30 on its external surface. As illustrated in particular in FIGS. 6 and 7, these radial shoulders 30 in the tubular piece 14, which is dilated radially by the press-fit of the rib 25 in the slot 29, cooperate with the radial shoulders 24 to hold the tubular piece 14 in the rear body 3 by elastic snap-fit. The rear edge 31 of the tubular piece 14 also forms a radial shoulder against which the lips 26, 27 of the segment 4 are supported accordingly to axially hold the front body 2 by elastic snap-fit, without however preventing it from rotating relative to the tubular piece 14 and the rear body 3. However, as illustrated in FIGS. 12 to 14, the tubular piece 14 also has axial protuberances on its front edge 32 forming stops 33 in rotation, which butt against the corresponding stop 28 of the front body 2 to limit the relative rotation of the rear body 3 relative to the front body 2. In this way, the tubular piece 14 axially connects the front body 2 and the rear body 3, and limits their relative rotation between the positions illustrated in FIGS. 2 and 3.

During assembly of the writing instrument 1, the slide 13 is introduced at the rear of the segment 4, and because of its radial elasticity the tubular piece 14 is threaded onto the rear end of the segment 4 until its rear edge 31 can be supported on the front faces of the lips 26. Next, the rear end of the segment 4, with the tubular piece 14 and the slide 13, is introduced into the rear body 3, with the slot 29 of the tubular piece 14 aligned with the rib 25 of the rear body 3, and the grooves 18, 19 of the slide 13 aligned with the corresponding ribs 16, 17 on the internal surface of the segment 4. Due to the radial elasticity of the tubular piece 14, and the inclination of the surfaces 34 and 35 respectively in the tubular piece 14 and the rear body 3, the rear end of the segment 4 and the tubular piece 14 can enter the front end of the rear body until the forced engagement of the rib 25 in the slot 29 causes radial dilation of the tubular piece 14, such that its radial shoulders 30 are supported on the radial shoulders 24 of the rear body 3 accordingly to block axially the segment 4 relative to the rear body 2. The refill 12 and the spring 11 can then be introduced into in the instrument 1 via the front end of the segment 4 which can then be closed with the end part 5 to complete the front body 2 and the instrument 1. Subsequently, the refill 12 could easily be replaced by unscrewing the end part 5 without having to separate the entire front body 2 from the rear body 3.

Although the present invention has been described in reference to a specific embodiment, it is evident that various modifications and changes could be made to these examples without departing from the general scope of the invention such as defined by the claims. Consequently, the description and the diagrams must be considered more illustratively than restrictively.

The invention claimed is:

1. A writing instrument comprising:

a front body with an ergonomic grasping segment asymmetrical relative to a first longitudinal plane, and a rear body asymmetrical relative to a second longitudinal plane, and capable of rotating relative to the ergonomic grasping segment of the front body about a longitudinal axis of rotation, between a position adapted to gripping with a right hand and a position adapted to gripping with a left hand, wherein the longitudinal axis of rotation is a line of intersection between the first longitudinal plane and the second longitudinal plane.

2. The writing instrument as claimed in claim 1, wherein said ergonomic grasping segment has, on one side of said first longitudinal plane, a rib oriented longitudinally, and radially projecting relative to a grasping surface of said segment.

3. The writing instrument as claimed in claim 2, wherein said rib is projecting by at least 2 mm relative to the grasping surface of said segment.

4. The writing instrument as claimed in claim 1, wherein said ergonomic grasping segment has a stop flange for fingers in the direction of a front end of the front body.

5. The writing instrument as claimed in claim 1, wherein said ergonomic grasping segment has a supple grasping surface.

6. The writing instrument as claimed in claim 5, wherein said supple grasping surface is overmoulded on the ergonomic grasping segment.

7. The writing instrument as claimed in claim 1, wherein said writing instrument also comprises: a writing point, and a retraction and extension mechanism of the writing point, actionable by relative rotation of the front and rear bodies, and configured such that the writing point is retracted in the front body when the rear body and the front body are in an intermediate position between the position adapted to gripping with the right hand and the position adapted to gripping with the left hand, and projecting beyond a front end of the front body when the rear body and the front body are in the position adapted to gripping with the right hand or in the position adapted to gripping with the left hand.

8. The writing instrument as claimed in claim 7, wherein the said retraction and extension mechanism comprises a cam surface secured in rotation with one of said front and rear bodies, and an element secured in rotation with the other of said front and rear bodies and in contact with said cam surface, the cam surface or the said element in contact with the cam surface being capable of moving inside the writing instrument along the said longitudinal axis and being secured to the writing point at least in translation along the longitudinal axis.

9. The writing instrument as claimed in claim 1, further comprising a tubular piece for axial joining of the front body with the rear body via elastic snap-fit.

10. The writing instrument as claimed in claim 9, wherein said tubular piece has radial shoulders opposite corresponding shoulders of the front and rear bodies for axial retaining of said tubular piece relative to said front and rear bodies.

11. The writing instrument as claimed in claim 9, wherein said tubular piece is received inside the writing instrument.

12. A writing instrument comprising:

a front body with an ergonomic grasping segment asymmetrical relative to a first longitudinal plane, a rear body asymmetrical relative to a second longitudinal plane, and capable of rotating relative to the front body about a longitudinal axis corresponding to a line of intersection between the first longitudinal plane and the second longitudinal plane, between a position adapted to gripping with a right hand and a position adapted to gripping with a left hand, and a tubular piece for axial joining of the front body with the rear body via elastic snap-fit, wherein said tubular piece is secured in rotation with one of said front and rear bodies and has two rotational stops relative to the other of said front and rear bodies.

13. The writing instrument as claimed in claim 9, wherein said tubular piece has a longitudinal slot.

14. A writing instrument comprising:

a front body with an ergonomic grasping segment asymmetrical relative to a first longitudinal plane, a rear body asymmetrical relative to a second longitudinal plane, and capable of rotating relative to the front body about a longitudinal axis corresponding to a line of intersection between the first longitudinal plane and the second longitudinal plane, between a position adapted to gripping with a right hand and a position adapted to gripping with a left hand, and a tubular piece for axial joining of the front body with the rear body via elastic snap-fit wherein said tubular piece has a longitudinal slot, and wherein said tubular piece, in said longitudinal slot, receives a rib secured to one of said front or rear bodies with which it is secured in rotation.

15. The writing instrument as claimed in claim 14, wherein the rib is press-fitted into the longitudinal slot.

16. The writing instrument as claimed in claim 1, wherein the ergonomic grasping segment is held between the tips of the thumb and at least one of the index finger or middle finger of one same hand, and the rear body is rotated relative to the front body towards the position adapted to gripping with a right hand or towards the position adapted to gripping with a left hand depending on the hand used, so as to ensure the supporting of the rear body in the grasping angle between the index finger and the thumb.

* * * * *